(12) United States Patent
Falk-Jordan

(10) Patent No.: US 9,494,563 B2
(45) Date of Patent: Nov. 15, 2016

(54) FITTING ELEMENT WITH BIO-COMPATIBLE SEALING

(75) Inventor: Stefan Falk-Jordan, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 767 days.

(21) Appl. No.: 13/811,655

(22) PCT Filed: Dec. 13, 2010

(86) PCT No.: PCT/EP2010/069537
§ 371 (c)(1),
(2), (4) Date: Jun. 6, 2013

(87) PCT Pub. No.: WO2012/010222
PCT Pub. Date: Jan. 26, 2012

(65) Prior Publication Data
US 2013/0298647 A1    Nov. 14, 2013

(30) Foreign Application Priority Data

Jul. 23, 2010    (GB) ................................. 1012342.0

(51) Int. Cl.
*G01N 30/00*    (2006.01)
*F16L 19/06*    (2006.01)
(Continued)

(52) U.S. Cl.
CPC ............ *G01N 30/00* (2013.01); *F16L 19/061* (2013.01); *F16L 19/07* (2013.01); *F16L 49/06* (2013.01);
(Continued)

(58) Field of Classification Search
CPC ................... F16L 19/061; F16L 19/07; F16L 49/06; G01N 30/6026; G01N 30/6039
(Continued)

(56) References Cited

U.S. PATENT DOCUMENTS 5,074,599 A * 12/1991 Wirbel .................... F16L 47/04
285/341
5,472,598 A    12/1995 Schick
(Continued)

FOREIGN PATENT DOCUMENTS

CN    201335820 Y    10/2009
DE    102008059897 A1    6/2010
(Continued)

OTHER PUBLICATIONS

Chinese Office Action dated Aug. 13, 2014.
Notification of Grant from related U.K. Application No. GB2482175.

*Primary Examiner* — John Fitzgerald

(57) ABSTRACT

A fitting element is configured for coupling tubing to a fluidic device having a receiving cavity configured for receiving the fitting element, where the tubing has an inner contact surface of a biocompatible material, the inner contact surface being configured to contact a fluid to be conducted by the tubing, and the receiving cavity having a receiving contact surface of a bio-compatible material. The fitting element includes a first sealing element of a bio-compatible material configured for sealing to the bio-compatible material of the inner contact surface of the tubing, and a second sealing element configured for sealing against a pressure ambient to a pressure of the fluid in the tubing. Upon coupling of the tubing to the fluidic device, at least a portion of the receiving contact surface, the first sealing element, and the second sealing element enclose an interspace, each surface of the interspace being a bio-compatible material.

29 Claims, 6 Drawing Sheets

(51) Int. Cl.
*F16L 19/07* (2006.01)
*F16L 49/06* (2006.01)
*G01N 30/60* (2006.01)

(52) U.S. Cl.
CPC ...... *G01N 30/6026* (2013.01); *G01N 30/6039* (2013.01)

(58) Field of Classification Search
USPC ........................................ 285/330, 399, 921
See application file for complete search history.

(56) References Cited

U.S. PATENT DOCUMENTS

| | | | |
|---|---|---|---|
| 5,651,885 A | 7/1997 | Schick | |
| 7,430,811 B2 * | 10/2008 | Williams | F16L 19/00 285/93 |
| 7,735,878 B2 * | 6/2010 | Keene | F16L 15/009 285/332 |
| 7,815,226 B2 * | 10/2010 | Williams | F16L 19/10 285/341 |
| 8,398,124 B2 * | 3/2013 | Bennett | F16L 19/065 285/389 |
| 8,931,808 B2 * | 1/2015 | Graham | G01N 30/6026 285/328 |
| 2002/0117855 A1 | 8/2002 | Rittenhouse | |
| 2004/0155458 A1 * | 8/2004 | Holmes, IV | F16L 37/0845 285/104 |
| 2005/0184521 A1 * | 8/2005 | Maguire | E21B 43/106 285/374 |
| 2008/0048446 A1 * | 2/2008 | Houghton | F16L 21/03 285/374 |
| 2011/0107823 A1 * | 5/2011 | Dehmer | F16L 19/061 73/64.56 |

FOREIGN PATENT DOCUMENTS

| | | |
|---|---|---|
| WO | 2007103464 A2 | 9/2007 |
| WO | 2010000324 A1 | 1/2010 |
| WO | 2011076244 A1 | 6/2011 |

\* cited by examiner

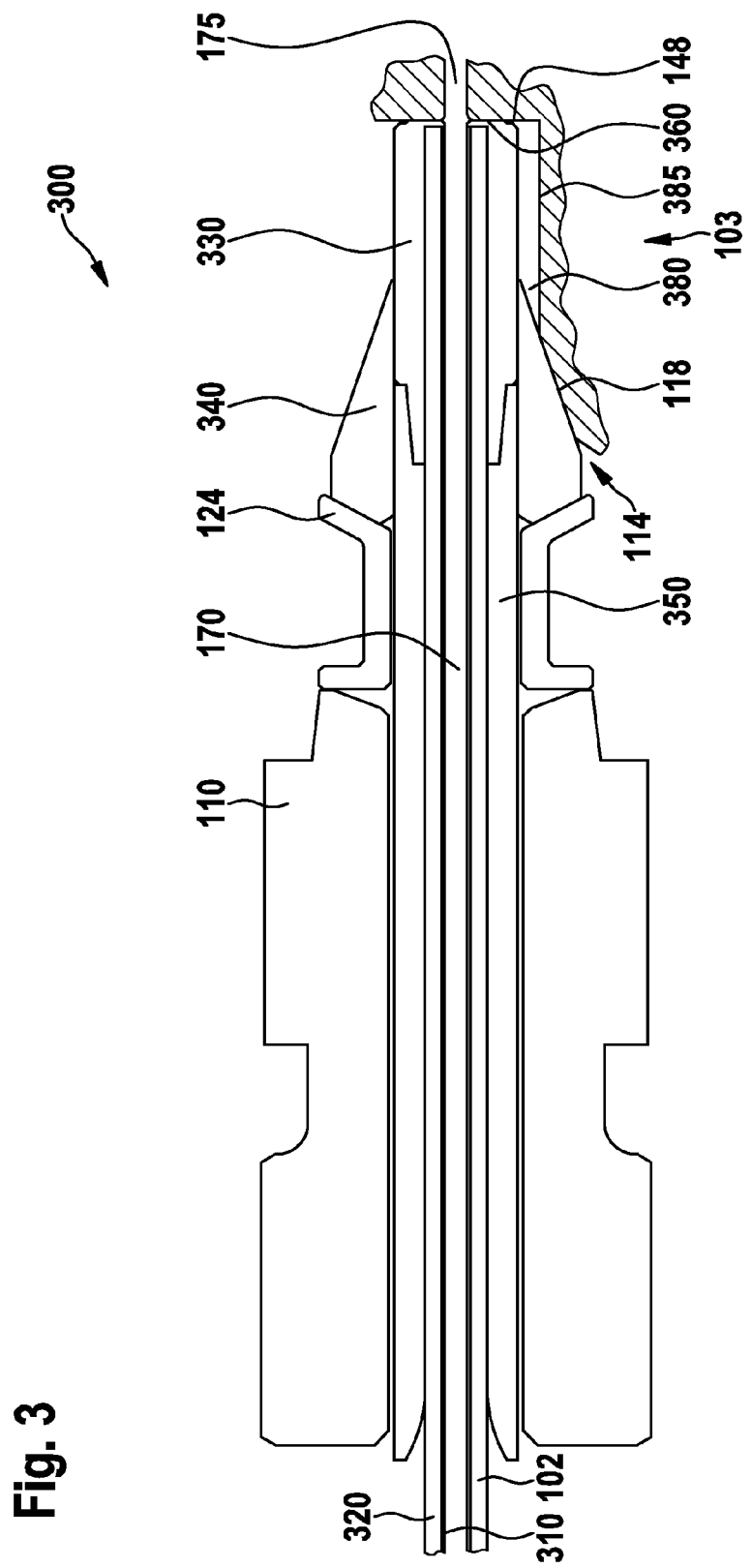

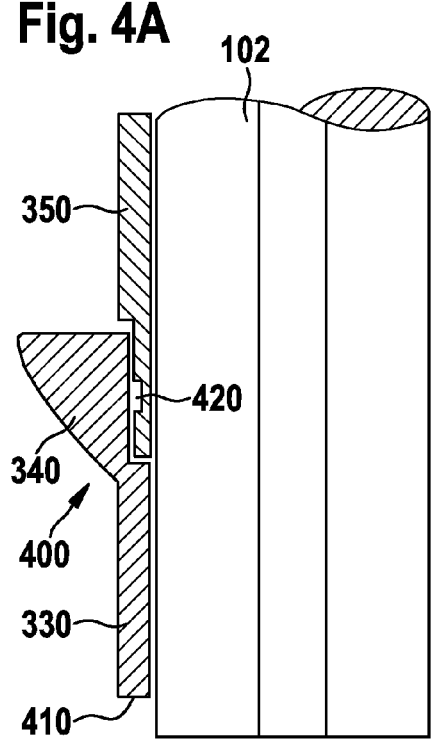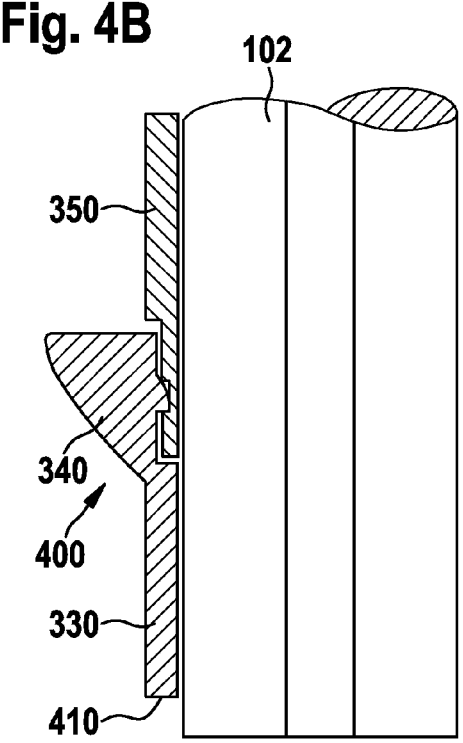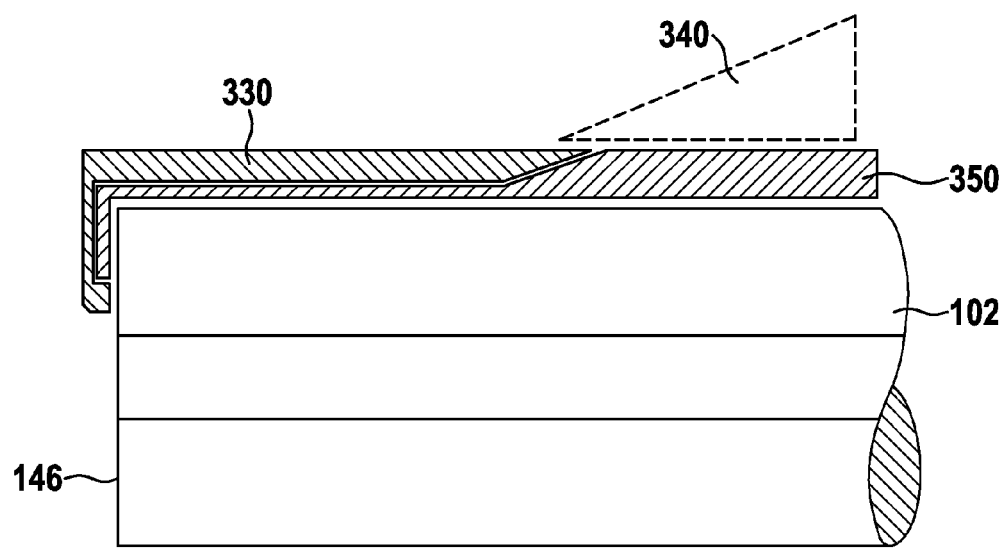

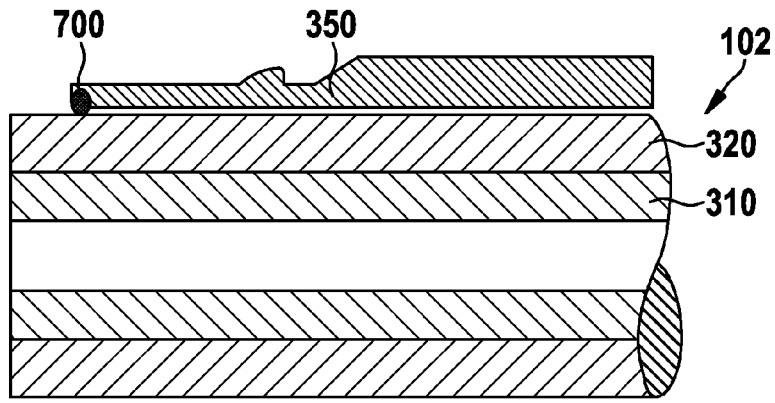
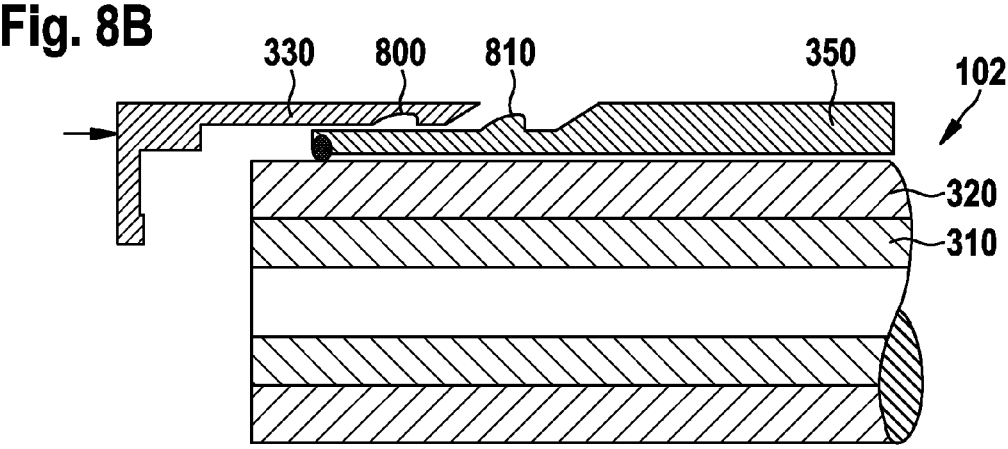
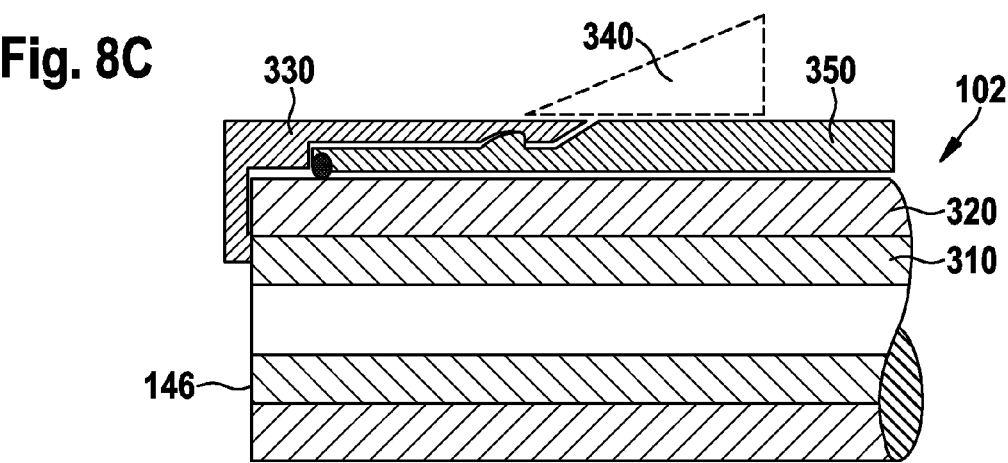

FITTING ELEMENT WITH BIO-COMPATIBLE SEALING

The present application is a U.S. national phase application under 35 USC §371(c) of International Application Pub. No. WO/2012/010222 filed on Dec. 13, 2010, naming S. Falk-Jordan as inventor. The entire disclosure of International Application Pub. No. WO/2012/010222 is hereby incorporated by reference in its entirety.

BACKGROUND

The present invention relates to a fitting element for a fluidic device, in particular in a high performance liquid chromatography application.

In high performance liquid chromatography (HPLC), a liquid has to be provided usually at a very controlled flow rate (e.g. in the range of microliters to milliliters per minute) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid with compounds to be separated is driven through a stationary phase (such as a chromatographic column), thus separating different compounds of the sample fluid which may then be identified.

The mobile phase, for example a solvent, is pumped under high pressure typically through a column of packing medium (also referred to as packing material), and the sample (e.g. a chemical or biological mixture) to be analyzed is injected into the column. As the sample passes through the column with the liquid, the different compounds, each one having a different affinity for the packing medium, move through the column at different speeds. Those compounds having greater affinity for the packing medium move more slowly through the column than those having less affinity, and this speed differential results in the compounds being separated from one another as they pass through the column.

The mobile phase with the separated compounds exits the column and passes through a detector, which identifies the molecules, for example by spectrophotometric absorbance measurements. A two-dimensional plot of the detector measurements against elution time or volume, known as a chromatogram, may be made, and from the chromatogram the compounds may be identified. For each compound, the chromatogram displays a separate curve or "peak". Effective separation of the compounds by the column is advantageous because it provides for measurements yielding well defined peaks having sharp maxima inflection points and narrow base widths, allowing excellent resolution and reliable identification of the mixture constituents. Broad peaks, caused by poor column performance, so called "Internal Band Broadening" or poor system performance, so called "External Band Broadening" are undesirable as they may allow minor components of the mixture to be masked by major components and go unidentified.

An HPLC column typically comprises a stainless steel tube having a bore containing a packing medium comprising, for example, silane derivatized silica spheres having a diameter between 0.5 to 50 µm, or 1-10 µm or even 1-7 µm. The medium is packed under pressure in highly uniform layers which ensure a uniform flow of the transport liquid and the sample through the column to promote effective separation of the sample constituents. The packing medium is contained within the bore by porous plugs, known as "frits", positioned at opposite ends of the tube. The porous frits allow the transport liquid and the chemical sample to pass while retaining the packing medium within the bore. After being filled, the column may be coupled or connected to other elements (like a control unit, a pump, containers including samples to be analyzed) by e.g. using fitting elements. Such fitting elements may contain porous parts such as screens or frit elements.

During operation, a flow of the mobile phase traverses the column filled with the stationary phase, and due to the physical interaction between the mobile phase and the stationary phase a separation of different compounds or components may be achieved. In case the mobile phase contains the sample fluid, the separation characteristics are usually adapted in order to separate compounds of such sample fluid. The term compound, as used herein, shall cover compounds which might comprise one or more different components. The stationary phase is subject to a mechanical force generated in particular by a hydraulic pump that pumps the mobile phase usually from an upstream connection of the column to a downstream connection of the column. As a result of flow, depending on the physical properties of the stationary phase and the mobile phase, a relatively high pressure occurs across the column.

Fittings for coupling different components, such as separation columns and conduits, of fluidic devices are commercially available and are offered, for instance, by the company Swagelok (see for instance http://www.swagelok.com). A typical tube fitting is disclosed in U.S. Pat. No. 5,074,599 A.

U.S. Pat. No. 6,494,500 discloses a self-adjusting high pressure liquid connector for use with high pressure liquid chromatography (HPLC) columns requiring liquid-tight and leak free seals between fittings and unions.

WO 2005/084337 discloses a coupling element comprising a male sealing element. The male sealing element may have a generally cylindrical shape, and defines a fluid passageway therethrough for the transmission of fluid. The male sealing element is secured to a ferrule which is located within a cavity of the nut. The coupling element also has a biasing element disposed between a retaining ring and the ferrule located within the nut cavity. This biasing element facilitates a fluid-tight, metal to metal (or metal to plastic, or plastic to plastic) seal between the male sealing element and female sealing element.

WO 2009/088663 A1 discloses liquid-chromatography conduit assemblies having high-pressure seals. A fluid-tight seal, proximal to the joint between two conduits, is provided, for example, through use of pressure, while a stabilizing seal, distal to the joint, is provided by adhering the conduits to the tube.

A high pressure connect fitting is disclosed at US 2008/0237112 A1. A tip of a seal contacts the walls of a tapered sealing cavity to form a primary seal. The volume of space between the very end of the tip and the end of a sealing cavity defines a dead space. As the seal is axially compressed within an annular recess, the tip engages the walls of the tapered sealing cavity to form the primary seal, and further deforms to occupy space otherwise associated with the dead space. As the tip of the seal engages the tapered sealing cavity, the end face of the seal compresses against the end of the annular recess to form a secondary seal extending radially around the tip of the seal.

U.S. Pat. No. 4,619,473 A describes a fluid passage connector for liquid chromatograph comprising a tube having a flat portion at one end and a seal seat surface. A similar device is known from the document "Viper Capillaries and Finger Tight Fitting System", Dionex, http://www.dionex.com/en-us/webdocs/78632_DS-Viper-Capillaries-17Jul2009-LPN2283.pdf.

WO 2010/000324 A1, by the same applicant, discloses a fitting for coupling a tubing to another component of a fluidic device. The fitting comprises a male piece having a front ferrule and a back ferrule both being slidable on the tubing. The male piece has a first joint element configured slidably on the tubing. A female piece has a recess configured for accommodating the front ferrule and the tubing, and a second joint element configured to be joinable to the first joint element. The back ferrule is configured in such a manner that, upon joining the first joint element to the second joint element, the back ferrule exerts a pressing force on the front ferrule to provide a sealing between the front ferrule and the female piece, and the back ferrule exerts a grip force between the male piece and the tubing.

International Patent Application PCT/EP2009/067646 discloses a fitting element configured for providing a fluidic coupling to a fluidic device. An inlay is located in a cavity of a front side of a tubing. The inlay protrudes over the front side, at least before coupling of the tubing to the fluidic device. Upon coupling of the tubing to the fluidic device, the front side is fitted to the fluidic device for connecting a fluid path of the tubing to a fluid path of the fluidic device, and the inlay provides a sealing of the fluid path of the tubing and the fluidic device.

A bio-compatible column for use in liquid chromatography applications is known from U.S. Pat. No. 5,651,885 A.

Fittings made of PEEK material are known e.g. from http://webstore.idex hs.com/Products/specsheet.asp?vSpecSheet=257&vPart=F-301&vFrom=L, which however only allow limited pressure application below 300-400 bar.

Ni-coated PEEK-Capillaries are disclosed at http://www.vici.com/tube/ni-cladpeek.php.

DISCLOSURE

It is an object of the invention to provide an improved fitting, in particular for HPLC applications requiring bio-compatibility.

According to the present invention, a fitting element is provided, which is configured for coupling a tubing to a fluidic device. The fluidic device has a receiving cavity configured for receiving the fitting element. The tubing has an inner contact surface comprised of a bio-compatible material, wherein the inner contact surface is configured to be in contact with a fluid to be conducted by the tubing. The receiving cavity has a receiving contact surface comprising a bio-compatible material. The fitting element comprises a first sealing element having a bio-compatible material and being configured for providing a sealing to the bio-compatible material of the inner contact surface of the tubing. The fitting element further comprises a second sealing element configured for sealing against a pressure ambient to a pressure of the fluid in the tubing. Upon coupling of the tubing to the fluidic device, at least a portion of the receiving contact surface, the first sealing element, and the second sealing element enclose an interspace, wherein each surface of the interspace is comprised of a bio-compatible material.

Embodiments of the invention allow providing a coupling between the tubing and the fluidic device which fulfills the requirements with respect to bio-compatibility. The two-stage sealing provided by the first and second sealing elements allows sealing the coupling between the tubing and the fluidic device even at higher pressure of the fluid to be conducted by the tubing. Embodiments may allow secure sealing at fluid pressure beyond 600 bar and even in the range of 1000-1500 bar and beyond. By providing the interspace being enclosed by bio-compatible surfaces only, the fitting element ensures a bio-compatible coupling of the tubing to the fluidic device even at higher pressure.

The bio-compatible material can be mainly used to avoid e.g. releasing ions from metal parts which may contaminate the sample and/or a column packaging material, and/or adversely affect the analysis itself.

The two-stage sealing provides a sealing in first stage where the tubing couples to the fluidic device, and an additional sealing stage in order to securely seal against a fluid pressure in the fluid path. In other words, the first sealing element may provide a low(er) pressure sealing (e.g. at the front side of the tubing), and the second sealing element may provide a high(er) pressure sealing located, for example, at or along a lateral side of the tubing.

It is to be understood that in particular the front side at the connection of the tubing to the fluidic device is often very difficult to seal, as in particular the shape of the counterpart element to the tubing might vary from one fluidic device to another and/or might have surface imperfections. However, contact pressure in particular in axial direction of the tubing might be limited in order to avoid or reduce destruction or deformation of the components involved. With increasing fluid pressure, for example in the range of thousand bar and beyond, conventional fitting systems have been often shown not to be sufficient and may lead to leaking and/or cross contamination. The two stage sealing, however, may allow that fluid even when "leaking" through the first stage of the first sealing element is fully sealed at the second stage and is limited from returning back into the fluid path, for example during normal application.

For example in an HPLC application, the front sealing provided by the first sealing element may allow fluid to pass ("leak") during pressurizing of the system (when the pressure in the system is raised to the desired target pressure). While the second sealing element fully seals so that no fluid can leak through such second sealing element, the interspace between the first and second sealing elements may become filled with fluid. However, as such fluid applied in the pressurizing phase in HPLC is normally only solvent which does not contain any sample, the interspace will thus be filled only with such (non-sample containing) solvent, so that no sample contamination can occur even when fluid contained in the inner space may return back into the fluid path. Further, it is to be understood that system pressure (after sample has been introduced) in HPLC usually changes slowly and within a narrow range compared to the system pressure, so that the fluid in the interspace is kept within the interspace and "sees" only very low "driving force" to communicate with the fluidic path of the inside of the tubing. Such embodiments thus provide a "chromatographic sealing" by the first sealing element (e.g. at the front side) and a "system pressure sealing" by means of the second sealing element. The term "chromatographic sealing" can be understood as a sealing sufficient during a sample run in an HPLC system, so that carry over (i.e. the sample is temporarily trapped and released later), or external band broadening (e.g. sample is guided to a "dead space" where the sample is released only by diffusion) can be avoided or at least limited, preferably while maintaining pressure within a narrow range when sample has been introduced in the HPLC-System.

In one embodiment, the first sealing element is configured for sealing the tubing in a region of an end of the tubing where the tubing is to be coupled to the fluidic device. In other words, the first sealing element provides a front-sided sealing at a front side of the tubing where the tubing abuts the receiving contact surface of the receiving cavity. Upon coupling of the tubing to fluidic device, the first sealing element may provide a first sealing stage at the front side of the tubing where the tubing is pressing to the receiving contact surface within the receiving cavity.

In embodiments, the first sealing element is comprised of the bio-compatible material. Each surface of the first sealing element may be comprised of the bio compatible material. Alternatively or in addition, each surface of the first sealing element, which may come in contact with the fluid to be conducted by the tubing, is comprised of the bio-compatible material.

In embodiments, the first sealing element is either removeably or fixedly coupled to the tubing. The first sealing element may be coupled to the tubing by at least one of: pressing, clipping, a direct molding process, a welding process, a gluing process, a thermal process (such as thermoforming), re-casting, re-melting, partial heating, laser heating, or ultra-sonic heating. It is clear that other ways or methods of coupling may be provided accordingly as long as fulfilling the requirements of either fixedly or removeably coupling the sealing elements to the tubing.

The first sealing element may at least partly cover a front side of the tubing, wherein the front side represents an axial end of the tubing. In such embodiments, the first sealing element may protrude in an axial direction (with respect to the tubing) over the front side of the tubing, at least before coupling of the tubing to the fluidic device. In alternative embodiments, upon coupling of the tubing to the fluidic device, the front side is fitted to the fluidic device for connecting a fluid path of the tubing to a fluid path of the fluidic device, and the first sealing element provides a sealing of the fluid path of the tubing and the fluidic device. Alternatively or in addition, upon coupling of the tubing to the fluidic device, the front side presses to a contact side of the fluidic device for coupling the fluid path of the tubing to the fluid path of the fluidic device. The first sealing element may laterally extend over the front side of the tubing. In such embodiment, the front side may represent a stopper for a forward motion of the tubing when the tubing is coupled to the fluidic device.

In one embodiment, the first sealing element comprises an outer surface which is facing the fluidic device upon coupling. The outer surface comprises a structure configured for increasing a surface pressure between the first sealing element and the fluidic device. The structure may comprise at least one of: one or more indentations (preferably concentric indentations), protrusions (preferably concentric protrusions), micro-cavities or inclusions for further acceptance of sealing components or impregnation.

Embodiments of the fitting element according to the invention provide a front-sided sealing of the tubing at the transition to the fluidic device. The sealing properties can be adapted and adjusted to the respective application, in particular by the design parameters such as material, size and shape of the fitting element or parts thereof (e.g. the inlay), and height e.g. of a protrusion over the front side of the tubing. By adequately selecting such design parameters, the fitting element will be pressed against the front side when the tubing is coupled to fluidic device, and will thus provide a sealing.

In case the first sealing element is provided of a material which can be deformed under the influence of pressure when coupling the tubing to the fluidic device, such as a polymer material (e.g. PEEK), the tubing may provide a stopper functionality, so that the first sealing element is only deformed until the front side is reached. In other words, deformation of the inlay will only occur until a protruding portion of the first sealing element has been deformed. This allows limiting the amount of deformation and allows ensuring that the fluid flow path is not excessively narrowed under the influence of continuing pressure.

In one embodiment, the first sealing element is or comprises an inlay located in a cavity of a front side of the tubing. Such cavity might be embodied in accordance as disclosed in the aforementioned International application PCT/EP2009/067646, which disclosure with respect to the inlay shall be incorporated herein by reference.

The inlay may protrude over the front side, at least before coupling of the tubing to the fluidic device. Upon coupling of the tubing to the fluidic device, the front side may be fitted to the fluidic device for connecting a fluid path of the tubing to a fluid path of the fluidic device, so that the inlay provides a sealing of the fluid path of the tubing and the fluidic device. The cavity may be located in a center position of the front side of the tubing and opening into the flow path of the tubing.

In preferred embodiments, the inlay is formed into the cavity, which cavity is preferably situated in the center of the front side of the tubing. The inlay may be form-fitted and/or pressed-fitted into the cavity. The inlay may be fixed into the cavity by applying a direct molding process, a welding process, a gluing process and/or thermal process. Such thermal process may be any or a combination of thermoforming, recasting, remelting, partial heating, laser heating, and ultrasonic heating. The inlay may be preformed (outside the cavity) and then inserted into the cavity. Alternatively, the inlay may also be directly formed into the cavity, e.g. by injection molding whereas the tubing has to be placed within the injection mold while injecting the polymeric material.

The inlay is preferably fixedly coupled into the cavity, and may result in an integral part to the tubing. This allows that the inlay stays fixed to tubing even when removing the tubing from the fluidic device after it has been coupled thereto. This can overcome a common problem in conventional fittings, such as in the aforementioned U.S. Pat. No. 4,619,473 type fittings, that a part of the fitting (in particular the front-sided sealing) may stick/remain in a receiving cavity of the fluidic device after removal of the fitting element. In applications e.g. where the inlay may (partly) remain in the receiving cavity after opening the fitting, the inlay may also be loosely inserted into the cavity. Alternatively, the inlay may be provided of a material, which allows that the inlay will be fixedly formed into the cavity under application of pressure when coupling the tubing to the fluidic device.

For fixedly coupling the inlay into the cavity, preferably a thermal process can be used, since a melting contact to the tubing may prevent gaps or voids which may cause further artifacts in liquid guiding, e.g. external band broadening or carry over.

In one embodiment, the inlay extends laterally over the cavity and at least partly onto the front side of the tubing. In other words, the inlay extends radially over the boundaries of the cavity, so that a portion of the inlay sits on at least a portion of the front side of the tubing. This combines the sealing properties of the inlay with a squeeze-type gasket but may also limit/reduce the stopper functionality provided by the tubing. In order to limit the sealing provided by the cavity to the front side only, the inlay may be laterally (or radially) limited to the front side only and thus not extend to the lateral side(s) of the tubing, e.g. in order to ensure that the tubing can be removed from the fluidic device after coupling.

In one embodiment the inlay only fills the cavity within the tubing, and the protrusion of the inlay deforms without lateral deformation into a gap between tubing and fluidic device, when being compressed.

In one embodiment, the inlay comprises a flow path, so that when the tubing is coupled to the fluidic device, the flow path of the inlay is (smoothly) coupled between the flow paths of the tubing and the fluidic device. In other words, the inlay provides a portion of the fluid flow path which guides the liquid and may thus reduce or eliminate disturbances. In one embodiment, the cavity is located in a center position of the front side of the tubing and opens into the flow path of the tubing.

In one embodiment, the inlay comprises an outer surface which is facing the fluidic device upon coupling. The outer surface may comprise a structure configured for increasing surface pressure between the inlay and the fluidic device when the tubing is coupled to the fluidic device. Such increasing of surface pressure may improve the sealing properties, for example by allowing withstanding of higher pressure. Further, such structure may also allow reducing the material (of the inlay) involved when tightened. In other words, by adequately designing the structure the material which has to be displaced under the influence of pressure for providing the desired sealing characteristic can be reduced. The structure may comprise one or more indentations, preferably (radially) concentric indentations, one or more protrusions, preferably (radially) concentric protrusions, one or more micro-cavities or other kind of inclusions for further acceptance of sealing components or impregnation, or any kind of combination thereof. Within these cavities or inclusions, a material different than that of the inlay can be fixed. Such material may be of lowered strength and/or increased formability and/or effect a wetting behavior (e.g. a hydrophobicity of liquid wetted surfaces).

In one embodiment, the inlay is made of or comprises a polymer material, such as PEEK, PEKK, PE, polyimide, a metal material such as gold, titanium, and SST20 alloys (preferably with low yield strength), and/or a ceramic such as $ZrO_2$, $Al_2O_3$, or Steatit. The material is preferably selected in order to adapt to an opposed surface of the fluidic device without leakage under a certain pressure drop. The inlay may also have a coating, such as gold, a polymer e.g. as a fluoropolymer, allowing covering and/or filling smaller surface roughness when being pressed. In case of a metal type inlay, (i.e. the inlay is comprised of a metal), a metal coating is preferably selected, such as gold. In case of a polymer type inlay, (i.e. the inlay is comprised of a polymer), a polymer coating is preferably selected, such as a fluoropolymer.

When applying a tubing having inner and outer tubings, the inlay can be configured to cover a contact region at an axial end of the tubing resulting where the inner and outer tubings are abutting together. Such contact region occurring at the front side of the tubing may show a gap between the inner and outer tubings or any other kind of surface irregularity and usually requires an extra step of closing such gap and/or surface irregularity. Often, certain surface irregularities still remain which may then lead to cross contamination, for example between different sample runs in HPLC. By designing the inlay to cover the axial end of the contact region, e.g. in that such contact region is within the cavity of the tubings, the inlay can close any surface irregularity and thus reduce or even avoid potential cross contamination.

In case the inner tubing is made of a bio-compatible material, such as a polymer (e.g. PEEK), and the outer tubing may be provided in particular for increasing mechanical strength but may not be bio-compatible at least as required, the inlay can be fixed to the inner tubing to become fluid tight. The cavity may then also be provided of a bio-compatible material, such as a polymer (e.g. PEEK), and seal the fluid against contacting the outer tubing, so that bio-compatibility of the tubing can be ensured. Fixing of the cavity to the inner tubing can be preferably achieved as aforedescribed, for example by a thermal process in particular by laser or ultrasonic heating.

In one embodiment, the first sealing element comprises a front socket surrounding the tubing in a region of an end of the tubing where the tubing is to be coupled to the fluidic device. The front socket comprises a bio-compatible material and provides the sealing to the bio-compatible material of the inner contact surface of the tubing.

The front socket may also comprise the second sealing element, so that the front socket provides the first sealing stage provided by the first sealing element as well as the second sealing stage provided by the second sealing element. Thus, the front socket may provide the first and second sealing elements in an integral component.

In one embodiment, the second sealing element provides—upon coupling of the tubing to the fluidic device—a second sealing stage for sealing the receiving cavity along a side of the tubing within the receiving cavity.

The second sealing element may comprise a front ferrule. The front ferrule may be slidable on the tubing at least before coupling the tubing to the fluidic device. The front ferrule may have a conically tapered front part configured to correspond to a conical portion of the receiving cavity of the fluidic device. Upon coupling of the tubing to the fluidic device, the conically tapered front part presses against the conical portion of the receiving cavity for sealing against the pressure of the fluid part of the tubing.

The second sealing element may be configured for sealing the receiving cavity of the fluidic device, when the receiving cavity receives the fitting element upon coupling of the tubing to the fluidic device. The first sealing element may be sealing the receiving cavity at the front side of the tubing, and the second sealing element may be sealing the receiving cavity along a side of the tubing within the receiving cavity.

In one embodiment, the fitting element further comprises a back socket surrounding the tubing in a region of an end of the tubing where the tubing is to be coupled to the fluidic device. The back socket is configured to provide mechanical support to the second sealing element exerting a force towards the tubing. The back socket thus allows providing sufficient mechanical support, which may be required for sealing of the second sealing element in particular in high pressure applications beyond 500 bar.

In one embodiment, the tubing comprises an inner tubing and an outer tubing. The outer tubing surrounds the inner tubing and provides mechanical support to the inner tubing. The inner tubing is comprised of a material different than the outer tubing. The inner tubing may comprise the bio-compatible material in order to ensure a biocompatible transport of the fluid. The outer tubing may comprise the first sealing element and/or the back socket.

In one embodiment the inner tubing is a tube-in-tube arrangement wherein the liquid leading tubing is made of fused silica or glass, and the second tubing covering the fused silica or glass tubing is made of metal or polymeric material.

In one embodiment, the second sealing element at least partly surrounds at least one of the front socket and the back socket.

In one embodiment, at least one bio-compatible material comprises at least one material of: a polymer (preferably PEEK, PEKK, PE, TEFLON® material (PTFE) and/or polyimide), a metal (preferably gold and/or titanium), and a ceramic.

The tubing may be made or comprise at least one of a group consisting of a metal, stainless steel, titanium, a plastic, a polymer, glass, quartz, and ceramic. The tubing may have a lumen having a diameter of less than 0.8 mm, particularly less than 0.2 mm. The tubing may have a circular, an elliptical or rectangular shape. The tubing may be or comprise a capillary.

In embodiments, the fitting element comprises a pre-load element configured for pressing—upon coupling of the tubing to fluidic device—the tubing in an axial direction of the tubing against the fluidic device. The pre-load element may be configured for pressing—upon coupling of the tubing to the fluidic device—a front side of the tubing in axial direction of the tubing against the fluidic device. The pre-load element may exert at least one of a spring-loaded and spring biased pressing force on the front side of the tubing. The pre-load element may be configured to promote—upon joining of the tubing and the fluidic device—a forward motion of the tubing towards the fluidic device. The pre-load element may be configured to promote—upon joining of the tubing and the fluidic device—a forward motion of the tubing towards a stopper of the tubing.

In one embodiment, the fitting element comprises a gripping element configured for promoting—upon coupling of the tubing to the fluidic device—a grip force to mechanically connect the gripping element with the tubing. Alternatively or in addition, the fitting element may comprise a first joint element configured for joining to the fluidic device, preferably by a screw connection.

In one embodiment, a fitting element is configured for coupling a tubing to a fluidic device. The tubing has an inner contact surface comprised of a bio-compatible material, and the inner contact surface is configured to be in contact with a fluid to be conducted by the tubing. The fitting element comprises a front socket and a back socket. The front socket and the back socket each surround the tubing in a region of an end of the tubing where the tubing is to be coupled to the fluidic device. The front socket comprises a bio-compatible material and provides a bio-compatible sealing to the bio-compatible material of the inner contact surface of the tubing. The back socket is configured to provide mechanical support to an outer fitting member exerting a force towards the tubing.

In one embodiment, a fitting is configured for coupling a tubing to a fluidic device. The tubing has an inner contact surface comprised of a bio-compatible material, and the inner contact surface is configured to be in contact with a fluid to be conducted by the tubing. The fitting comprises a fitting element according to any of the aforementioned embodiments. The fluidic device comprises a receiving cavity configured for receiving the fitting element. The receiving cavity comprises a receiving contact surface comprising a bio-compatible material. Upon coupling of the tubing to the fluidic device, the first sealing element provides a sealing to the bio-compatible material of the inner contact surface of the tubing, the second sealing element seals against a pressure ambient to a pressure of the fluid in the tubing, and a fluid part of the tubing is connected to a fluid path of the fluidic device.

In one embodiment, the fitting element comprises a pre-load element, a gripping element, and a first joint element. The receiving cavity comprises a second joint element. Upon coupling of the tubing to the fluidic device, the pre-load element presses the tubing in an axial direction of the tubing against the fluidic device, the gripping element promotes a grip force to mechanically connect the gripping element with the tubing, and the first joint element joins to the second joint element of the fluidic device.

The fluidic device may be or comprise at least one of: a second tubing, an apparatus, an HPLC device, a fluid separation device, a fluid handling device, a measurement device, etc.

The fluidic device may comprise a processing element configured for interacting with a sample fluid.

The fluidic device may be configured to conduct a sample fluid through the fluidic device, and/or to analyze at least one of a physical, chemical or biological parameter of at least one compound of a sample fluid. The fluidic device might be configured as a fluid separation system for separating compounds of a sample fluid and/or a fluid purification system for purifying a sample fluid.

The terms "radial" and "axial", as used herein, shall be defined with respect to the tubing having an axial direction in the direction of the fluid flow and a radial direction perpendicular to the axial direction. The tubing extends in axial direction, and the flow path of the tubing is radially enclosed by the tubing.

The terms "fitting" and "fitting element", as used herein, shall both relate to coupling a tubing to a fluidic device. The term "fitting" shall cover all components required for coupling the tubing to the fluidic device, and may even comprise the tubing and/or the fluidic device, or parts thereof. The term "fitting element" shall cover a part of the fitting.

An embodiment of the present invention comprises a fluid separation system configured for separating compounds of a sample fluid in a mobile phase. The fluid separation system comprises a mobile phase drive, such as a pumping system, configured to drive the mobile phase through the fluid separation system. A separation unit, which can be a chromatographic column, is provided for separating compounds of the sample fluid in the mobile phase. The fluid separation system further comprises a fitting element and/or fitting as disclosed in any of the aforementioned embodiments for coupling a tubing (provided the conducting the mobile phase) to a fluidic device in such fluid separation system. The fluid separation system may further comprise a sample injector configured to introduce the sample fluid into the mobile phase, a detector configured to detect separated compounds of the sample fluid, a collector configured to collect separated compounds of the sample fluid, a data processing unit configured to process data received from the fluid separation system, and/or a degassing apparatus for degassing the mobile phase. The fluidic device to which the tubing is or can be coupled can be any of such devices, and plural of such fittings or fitting elements may be used within such fluid separation system.

Embodiments of the present invention might be embodied based on most conventionally available HPLC systems, such as the Agilent 1200 Infinity Series, or the Agilent 1100 HPLC series (all provided by the applicant Agilent Technologies—see www.agilent.com—which shall be incorporated herein by reference).

The separating device preferably comprises a chromatographic column providing the stationary phase. The column might be a glass, plastic material or steel tube (e.g. with a diameter from 50 μm to 5 mm and a length of 1 cm to 1 m)

or a microfluidic column (as disclosed e.g. in EP 1577012 or the Agilent 1200 Series HPLCChip/MS System provided by the applicant Agilent Technologies, see e.g. http://www.chem.agilent.com/Scripts/PDS.asp?1Page=38308).

The mobile phase (or eluent) can be either a pure solvent or a mixture of different solvents. It can be chosen e.g. to minimize the retention of the compounds of interest and/or the amount of mobile phase to run the chromatography. The mobile phase can also been chosen so that the different compounds can be separated effectively. The mobile phase might comprise an organic solvent like e.g. methanol or acetonitrile, often diluted with water. For gradient operation water and organic is delivered in separate bottles, from which the gradient pump delivers a programmed blend to the system. Other commonly used solvents may be isopropanol, THF, hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The fluid is preferably a liquid but may also be or comprise a gas and/or a supercritical fluid (as e.g. used in supercritical fluid chromatography—SFC—as disclosed e.g. in U.S. Pat. No. 4,982,597 A).

The pressure in the mobile phase might range from 2-200 MPa (20 to 2000 bar), in particular 10-150 MPa (100 to 1500 bar), and more particularly 50-120 MPa (500 to 1200 bar).

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s). The illustrations in the drawings are schematic.

FIG. 3 shows in more detail an exemplary embodiment of fitting components 300 of the fitting 100.

FIGS. 4-8 illustrate various embodiments in schematic cross-sectional part view.

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

Figure 1:
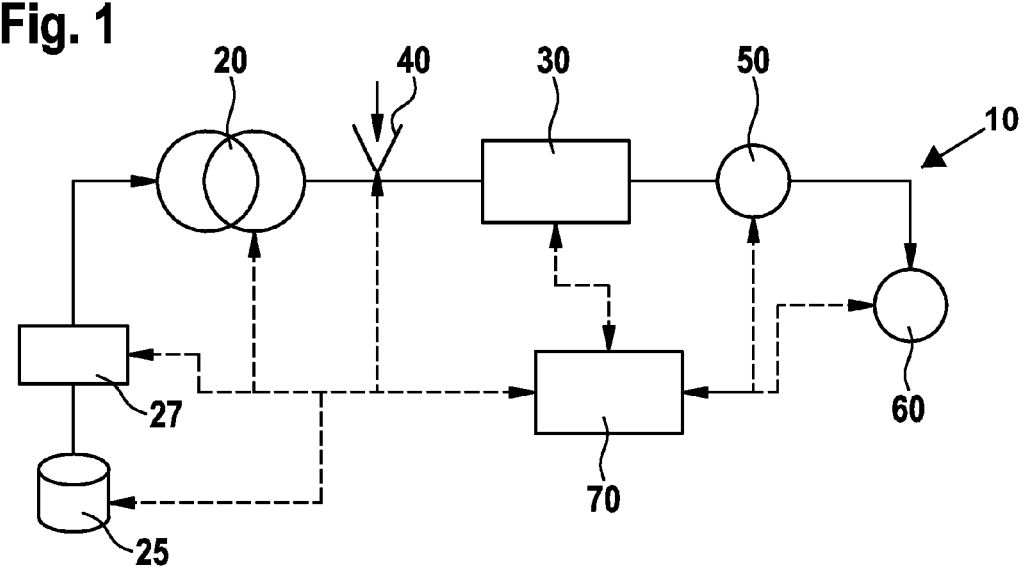
FIG. 1 shows in schematic view a liquid separation system 10, in accordance with embodiments of the present invention, e.g. used in high performance liquid chromatography (HPLC).

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization of sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provide data back.

For transporting liquid within the liquid separation system 10, typically tubings (e.g. tubular capillaries) are used as conduits for conducting the liquid. Fittings are commonly used to couple plural tubings with each other or for coupling a tubing to any device. For example, fittings can be used to connect respective tubings to an inlet and an outlet of the chromatographic column 30 in a liquid-sealed fashion. Any of the components in the fluid path (solid line) in FIG. 1 may be connected by tubings using fittings. While the fluid path after the column 30 is usually at low pressure, e.g. 50 bar or below, the fluid path from the pump 20 to the inlet of the column 30 is under high pressure, currently up to 1200 bar, thus posing high requirements to fluid tight connections.

Figure 2:
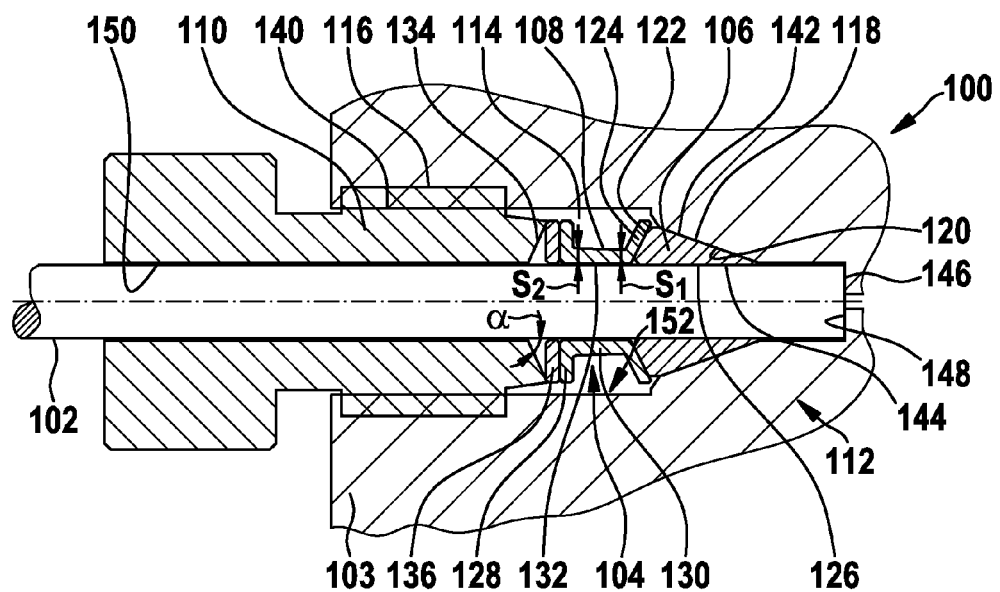
FIG. 2 illustrates a cross-sectional view of a fitting 100 according to an exemplary embodiment.

FIG. 2 shows an embodiment of a high pressure fitting 100 for coupling a tubing 102 (having a (not shown) inner fluid channel for conducting liquid, e.g. the mobile phase with or without a sample fluid) to another fluidic device 103, such as chromatographic column 30 of FIG. 1. In the schematic view of FIG. 2, only the portion of the device 103 which is relevant for the coupling with the tubing 102 is depicted.

The fitting 100 comprises a male piece 104 having a front ferrule 106 (e.g. made of a polymer material) and having a back ferrule 108 (e.g. made of a metallic material). The front ferrule 106 and the back ferrule 108 are integrally formed and are slidable together over the tubing 102 (which might have a metal outer tubing or socket as shown later in greater detail). Moreover, the male piece 104 has a first joint element 110 configured slidably on the tubing 102. Thus, for mounting the fitting 100 on the tubing 102, the integrally formed configuration of the front ferrule 106 and the back ferrule 108 is slid over the tubing 102, and subsequently the first joint element 110 is slid on the tubing 102. The front ferrule 106, the back ferrule 108 and the first joint element 110 together constitute the male piece 104.

After having slid the male piece 104 over the tubing 102, a female piece 112 having a receiving cavity 114 (e.g. a recess) may be slid over the tubing 102 from the right-hand side to the left-hand side of FIG. 2. The female piece 112 has the receiving cavity 114 configured for accommodating the front ferrule 106, the back ferrule 108, a part of the first joint element 110, and the tubing 102, and has a second joint element 116 configured to be joinable to the first joint element 110. The first and the second joint elements 110, 116 may be fastened to one another by a screw connection, as will be explained below in more detail.

A lumen 126 of the front ferrule 106 is dimensioned for accommodating the tubing 102 with clearance. A lumen 132 of the back ferrule 108 is dimensioned for accommodating the tubing 102 with clearance. The first joint element 110 also has a lumen 150 configured for accommodating the tubing 102 with clearance.

The back ferrule 108 is configured such that upon joining the first joint element 110 to the second joint element 116, the back ferrule 108 exerts a pressing force on the front ferrule 106 to provide a sealing between the front ferrule 106 and the female piece 112. Simultaneously, such joining has the consequence that the back ferrule 108 exerts a grip force between the male piece 104 and the tubing 102, and that the front ferrule 106 is sealed against the tubing 102 to prevent any fluid leakage. The pressing force has a direction which is longitudinal (parallel to an extension of the tubing 102), whereas the grip force has a direction which is perpendicular to the extension of the tubing 102. As the grip force, the back ferrule 108 generates a positive locking force between the male piece 104 and the tubing 102. This prevents the tubing 102 from laterally sliding after having fixed the two joint elements 110, 116 to one another.

As can be taken from FIG. 2, the front ferrule 106 has a conically tapered front part 118 shaped and dimensioned to correspond to a conical portion 120 of the receiving cavity 114 of the female piece 112. Thus, a form closure between the conical portion 120 of the receiving cavity 114 on the one hand and the conically tapered front part 118 of the front ferrule 106 may be achieved. Moreover, the front ferrule 106 has a conically tapered back part 122 (which may also be arranged vertically or upright) shaped and dimensioned to correspond to a slanted annular front spring 124 of the back ferrule 108. Although the shapes of the two components 122, 124 are adjusted to match to one another, it is nevertheless possible that upon exertion of corresponding forces, the slanted annular front spring 124 is bent. The slanted annular front spring 124 is adapted for being bent, upon joining the first joint element 110 to the second joint element 116, into an upright position (see arrow 152) to promote a forward motion of the front ferrule 106 towards a stopper portion 148 which is a receiving contact surface (or part of a receiving contact surface) of the receiving cavity 114 of the female piece 112.

An annular back spring 128 is provided as part of the back ferrule 108 which is adapted to promote, upon joining the first joint element 110 to the second joint element 116, a forward motion of the tubing 102 towards a stopper portion 148 of the receiving cavity 114 of the female piece 112 providing a spring-loading force.

Between the annular back spring 128 and the slanted annular front spring 124 (two disk springs), a sleeve element 130 (a flat spring) is arranged. The sleeve element 130 is conically tapered and has a thicker portion facing the first joint element 110 and has a thinner portion facing the front ferrule 106. A thickness s1 of the thinner portion is smaller than a thickness s2 of the thicker portion. These different thickness values allow the sleeve element 130 to improve the force distribution in a longitudinal direction of FIG. 2.

The first joint element 110 is configured for being joined to the second joint element 116 by a screw connection. Thus, in a portion 140, an internal thread of the female piece 112 can be screwed into an external thread in the first joint element 110 of the male piece 104. A user simply has to fasten this screwing connection, and thereby automatically seals the front ferrule 106 against the female element 112 and exerts a grip between the back ferrule 108 and the tubing 102.

A slanted surface 134 of the first joint element 110 is configured for exerting a bending moment onto the annular back spring 128 of the back ferrule 108. The slanted surface 134 includes an acute angle $\alpha=60°$ with an outer surface of the tubing 102. With such an acute angle $0 \leq \alpha \leq 90°$, a desired bending of the annular back spring 128 and the sleeve element 130 of the back ferrule 108 and of an optional additional spring 136 may be effected. As an alternative to the described configuration, it is possible that the annular back spring 128 is slanted and the annular front spring 124 is upright, or that both the annular back spring 128 and the annular front spring 124 are slanted in a way that both of them include an acute angle with the sleeve element 130.

A force transmitting annular metal ring 136 (which supports additional force to the front ferrule 106 without increasing radial grip on tubing 102) is arranged slidable on the tubing 102 between the back ferrule 108 and the first joint element 110, and transmits a force exerted by the first joint element 110 to the back ferrule 108. The force transmission element 136 operates as a washer disk and is provided as a separate element which is not integrally formed with a front ferrule 106 and a back ferrule 108. The additional metal ring 136 may be added to increase the sealing force and the elastic deformation independent of the supplied gripping force.

FIG. 2 shows a non-biased state of the fitting 100. In a sealed configuration, a first seal connection is achieved in a sealing region 142 between the front ferrule 106 and the female part 112, and a second sealing connection is achieved in a sealing region 144 between the front ferrule 106 and the tubing 102. In a front side (or frontal area) 146 of the tubing 102, is optionally possible to provide a polymeric coating in order to further suppress sample contamination, since this measure may further increase the sealing performance between the front side 146 and the stopper portion 148.

In the following, the force transmission will be explained: After having slid the front ferrule 106 and the back ferrule 108 on the tubing 102 and after having slid the first joint element 110 onto the tubing 102, the first joint element 110 may be connected by screwing with the second joint element 116. This converts the back ferrule 108 into a biased state so that grip is generated between the tubing 102 and the back ferrule 108. As the grip force increases the force longitudinal to the capillary axis increases analog and supplies pressure to the sealing regions 142, 144. A corresponding force transmission further results in an upward pivoting of the annular front spring 124 of the back ferrule 108, as indicated by arrow 152. This presses the polymer material of the front ferrule 106 to a frontward position, i.e. towards the right-hand side of FIG. 2 and supplies pressure to the sealing regions 142, 144.

FIG. 3 shows in more detail an exemplary embodiment of fitting components 300 of the fitting 100, which are coupled with the tubing 102. In other words, the device 103 (as depicted in FIG. 2) is omitted in FIG. 3 for the sake of clearer representation.

In the embodiment of FIG. 3, the tubing 102 has an inner tubing 310 and outer tubing 320. The outer tubing 320 surrounds the inner tubing 310 and provides mechanical support to the inner tubing 310. The inner tubing 310 is typically comprised of a material different from the outer tubing 320. In this embodiment, the inner tubing 310 comprises a bio-compatible material, such as PEEK. The inner tubing 310 includes an inner contact surface (as indicated by the lead line for reference numeral 310) configured to contact a fluid to be conducted by the inner tubing 310, i.e., the surface facing the interior of the inner tubing 310. The inner contact surface may thus also comprise the bio-compatible material. In order to provide sufficient mechanical support for the inner tubing 310, the outer tubing 320 in this embodiment shall comprise a nickel material, such as the aforementioned Ni-coated peak capillaries as referred to in the introductory part of the description. inner contact surface comprising a biocompatible material, the inner contact surface is being configured to contact a fluid to be conducted by the tubing The tubing-sided fitting components 300 of the embodiment of FIG. 3 further comprise a first sealing element 330 (also acting as a front socket), a second sealing element 340, a back socket 350, the annular front spring 124, and the first joint element 110. The first sealing element 330 here is embodied as a front socket.

Further in FIG. 3 a portion of the receiving cavity 114, to which the tubing sided fitting elements 300 are abutting to, is also schematically illustrated.

The first sealing element 330 also comprises a bio-compatible material, for example PEEK, and closely seals to the inner tubing 310, thus providing a biocompatible material transition between the bio-compatible material of the inner tubing 310 and the bio-compatible material of the first sealing element 330. This can be achieved, for example, by having the polymers overlapping in the transitional area.

A front side 360 of the first sealing element 330 is abutting to the stopper portion 148 of the receiving cavity 114. This provides a front-sided sealing for the tubing 102 for sealing a fluid path 170 of the tubing 102 to a fluid path 175 of the fluidic device 103.

The second sealing element 340 is provided and embodied here by a front ferrule, which may be slidably attached to the tubing 102. The second sealing element 340 abuts to the conically tapered front part 118 of the receiving cavity 114 and thus provides a second sealing stage for sealing against a pressure ambience to a pressure of the fluid in the fluid paths 170, 175.

The illustration in FIG. 3 shows a state where the tubing 102 is coupled to the fluidic device 103 for sealingly coupling the tubing 102 with the fluidic device 103. The schematic representation in FIG. 3 shows that an interspace 380 results where the front side 360 abuts to the stopper portion 148 and the second sealing element 340 abuts to the tapered front part 118. It is clear that the representation of the interspace 380 in FIG. 3 is only schematic and that the actual size of the interspace 380 is typically much smaller and mainly depends on tolerances of the tubing 102 and the receiving cavity 103.

In operation, when the tubing 102 is conducting a fluid (e.g. a liquid) under high pressure, for example 500 bar and beyond, a portion of such fluid might leak through the front side 360 into the interspace 380. The two sealing stages provided by the front side 360 and the second sealing element 340 are preferably configured that under normal conditions, i.e. when the tubing 102 is securely coupled to the receiving cavity 103, the second sealing stage of the second sealing element 340 fully seals against the ambient of the interspace 380, so that any liquid will not leak from the interspace 380 to such ambient. However, more importantly, it is to be understood that under the influence of pressure variation, liquid from within the interspace 380 might leak back into the fluid path 170, 175, for example when the pressure in the fluid path 170, 175 falls below pressure in the interspace 380. In order to ensure bio-compatibility of the coupling, the interspace 380 has to be configured so as not to provide any surface which might interfere with the requirement of bio-compatibility. For that purpose, each surface of the interspace 380 comprises a bio-compatible material. In the embodiment of FIG. 3, this means that at least the stopper portion (or receiving contact surface) 148, the tapered front part 118 and an area 385 in between the stopper portion 148 and the front part 118, the surface of the second sealing element 340 facing the front part 118, and the surface of the first sealing element 330 facing into the interspace 380, and the front side 360 have to be provided with a surface of a bio-compatible material. Accordingly, any fluid from within the interspace 380, which might leak back into the flow path 170, 175 will not adversely affect the required bio-compatibility. At the same time, the two-stage sealing provided by the first and second sealing elements 330 and 340 allows designing the fitting 100 to be suitable even for high pressure applications beyond 500 bar and even up to 1000 bar and beyond.

FIGS. 4-8 illustrate various embodiments in schematic cross-sectional part view. For the sake of simplicity, the given embodiments only show such components and views relevant for such embodiment, and the Figures also only depict partial views illustrating only one side of the three-dimensional embodiments. It is clear that the embodiments are typically rotationally and/or axially symmetric.

In the embodiment of FIGS. 4A and 4B, the tubing 102 is a PEEK capillary. The first sealing element 330 and the second sealing element 340 are provided in one component as a front ferrule 400, which shall also be made of PEEK. The front ferrule 400 can also extend over the tubing 102 and seal the front side of the tubing as will be shown in FIG. 5.

To provide sufficient mechanical stability, the embodiments of FIGS. 4A and 4B further comprise the back socket 350, which is preferably made of a metal material such as stainless steel (SST), titanium, ceramic or other mechanically resistant materials. The back socket 350 and front socket 400 are designed so that at least a portion of the back socket 350 is situated between the conically shaped second sealing element 340 and the capillary 102, (at least) when assembled in the receiving cavity 114 (not shown in FIG. 4), so that the back socket 350 can take up a radial force resulting from the second sealing element 340 being pressed against the conically shaped side 118 of the receiving cavity 103 (as depicted in FIG. 3). The back socket 350 may provide a clearing recess 420, into which material of the second sealing element 340 may flow under the influence of the radial force, thus providing a form-fit between the front socket 400 and the back socket 350. Such form-fitting may occur at the first assembly and fastening of the fitting 100 (see FIG. 2) in order to ensure safe removing of all parts when disassembling the tubing 102 from the fitting 100. The back socket 350 may be welded to the capillary 102 and thus be provided fixed with respect to the capillary 102, while the front socket 400 may be provided slidable on the tubing 102 and then be fixed to the back socket 350 by means of the recess clearance 420.

In the embodiment of FIG. 5, the capillary 102 shall also be made of a bio-compatible plastic material, such as PEEK, and the back socket 350 is made of a material providing sufficient mechanical support, such as a metal material. In the example of FIG. 5, the back socket 350 extends up to and over the front side 146 of the tubing 102. The back socket 350 is preferably fixedly coupled with the tubing 102, for example, by a gluing or welding process. The first sealing element 330 is provided as a front socket and may be slid over the back socket 350 and then fixedly coupled to the back socket 350, for example, by a gluing or welding process. The first sealing element 330 extends beyond and over the back socket 350 at the front side 146. Sealing of non-biocompatible material can be ensured e.g. by pressing of the tubing 102 together with the back socket 350 against the first sealing element 330, acting as a front socket. The second sealing element 340, indicated in FIG. 5 by a dotted line, may here be an individual component or an integral part of the first sealing element 330, for example in accordance with the embodiment shown in FIGS. 4A and 4B.

Figure 6:
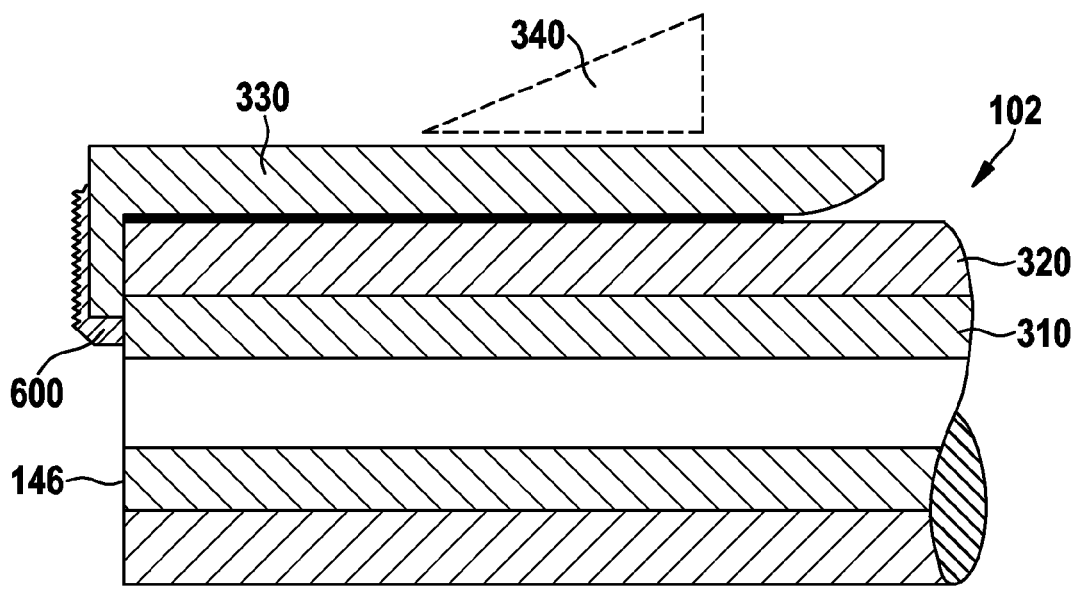

In the embodiment of FIG. 6, the tubing 102 comprises the inner tubing 310 and the outer tubing 320 in accordance with the embodiment of FIG. 3. The inner tubing 310 may be made of PEEK with the outer tubing 320 being a metal material such as nickel. The first sealing element 330 is embodied as a front socket and extends over the lateral side of the tubing 102 up to and at least partly over the front side 146 of the tubing 102. The first sealing element 330 extends at the front side 146 at least up to the inner tubing 310 and seals thereto.

In the embodiment of FIG. 6, the first sealing element 330 may further comprise an inlay 600, which can be embodied e.g. as disclosed in the aforementioned International application PCT/EP2009/067646. The inlay 600 may be made of a material such as e.g. PEEK, PTFE.

Alternatively to the inlay 600, a cutting ring (not shown) can be used, which cuts into the inner tubing 310 e.g. upon mounting of the first sealing element 330 and the tubing 102.

Figure 7A:
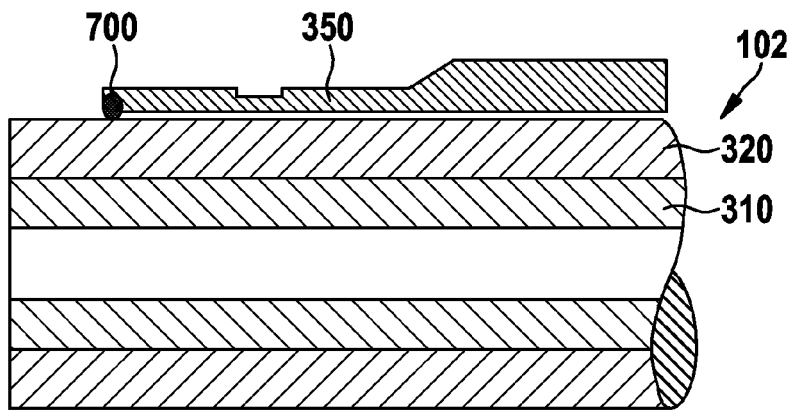
Figure 7B:
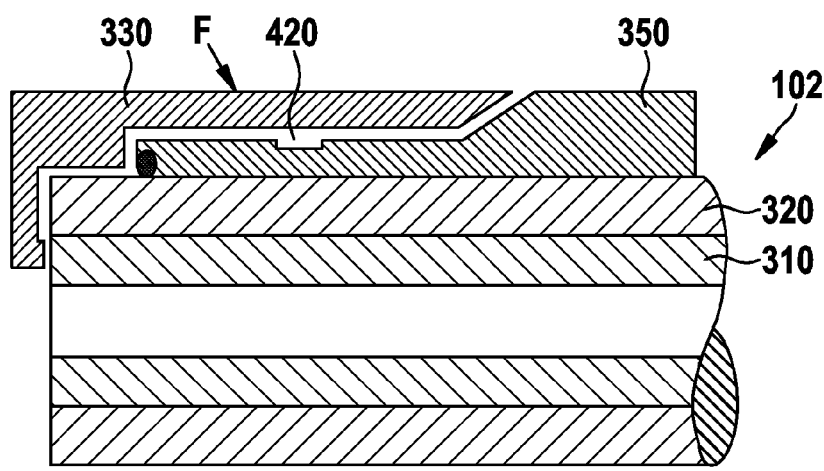
Figure 7C:
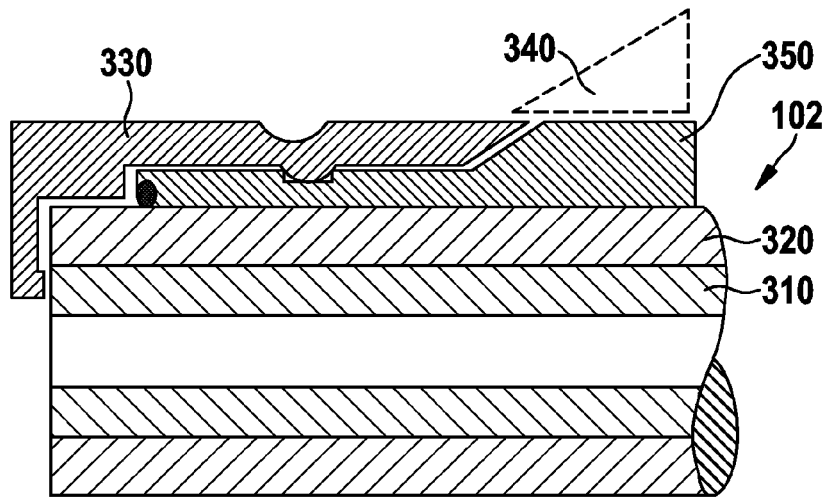

In the embodiment of FIGS. 7A-7C, the capillary 102 will also comprise the inner tubing 310 and the outer tubing 320, with the inner tubing 310 being made of a bio-compatible material, such as PEEK, and the outer tubing 320 providing mechanical support and being made, for example, of metal such as nickel or stainless steel. The back socket 350 is made here of a metal material and fixedly coupled to the outer tubing 320, for example, by a welding process as indicated by a weld seam 700.

In FIG. 7B, the first sealing element 330 is provided (again) in form of a front socket and shall be made of a bio-compatible polymer material, such as PEEK. The first sealing element 330 is slid over the front-sided end of the tubing 102 and at least partly extending over the front side 146 of the tubing 102, at least until reaching the inner tubing 310. Alternatively, a cutting ring (not shown) can be used, which cuts into the inner tubing 310, e.g. upon mounting of the first sealing element 330 and the tubing 102, thus sealing against the outer tubing 320.

Similar to the embodiment shown in FIG. 4A, the back socket 350 in FIGS. 7A-7C also comprises a recess clearance 420. When applying a force (as indicated in FIG. 7B by arrow F) onto the first sealing element 330, the first sealing element 330 can be deformed for at least partly filling the recess clearance 420, as indicated in FIG. 7C, in order to provide a form fit between the first sealing element 330 (front socket) and the back socket 350.

The embodiment of FIGS. 8A-8C substantially corresponds to the embodiment of FIGS. 7A-7C, with the tubing 102 also comprising a bio-compatible inner tubing 310 and a support providing outer tubing 320. The back socket 350, made of a metal material, shall also be fixedly coupled to the outer tubing 320, for example, by a welding process (indicated by weld seam 700).

Similar to FIG. 7B, the first sealing element 330 is slid in axial direction (as indicated by the arrow) over the tubing 102 and partly over the back socket 350. The first sealing element 330 comprises a first locking feature 800, which in combination with a second locking feature 810 of the back socket 350 provides a locking, such as a snap fit of the first sealing element 330 to the back socket 350, when the first sealing element 330 is slid in place (as depicted in FIG. 8C).

In the position of FIG. 8C, the first sealing element 330 extends over the front side 146 of the tubing 102 and seals to the inner tubing 310.

Further in FIG. 8C, the second sealing element 340 can be designed to at least partly reach over the first and second locking element 800 and 810 in order to provide a pressing force in radial direction to securely couple the first sealing element 330 with the back socket 350 for example by a form fitting.

In the embodiments of FIGS. 5-8, the conically shaped second sealing element 340 may be provided as an individual component, such as a front ferrule, as indicated by the dotted line, or may be integrally embodied with either the first sealing element 330 or the back socket 350.

The invention claimed is:

1. A fitting element configured for coupling a tubing to a fluidic device, the fluidic device comprising a receiving cavity configured for receiving the fitting element, wherein the tubing comprises an inner contact surface comprising a biocompatible material, the inner contact surface is configured to contact a fluid to be conducted by the tubing, and the receiving cavity comprises a receiving contact surface comprising a bio-compatible material, the fitting element comprising:
    a first sealing element comprising a bio-compatible material and being configured for sealing to the bio-compatible material of the inner contact surface of the tubing; and
    a second sealing element configured for sealing against a pressure ambient to a pressure of the fluid in the tubing, wherein, upon coupling the tubing to the fluidic device via the fitting element, at least a portion of the receiving contact surface, the first sealing element, and the second sealing element enclose an interspace, each surface of the interspace comprising a bio-compatible material.

2. The fitting element of claim 1, wherein the first sealing element is configured for sealing the tubing in a region of an end of the tubing where the tubing is to be coupled to the fluidic device.

3. The fitting element of claim 1, wherein, upon coupling the tubing to the fluidic device, the first sealing element provides a sealing stage at a front side of the tubing where the tubing is pressing to the receiving contact surface within the receiving cavity.

4. The fitting element of claim 1, wherein each surface of the first sealing element configured to come in contact with the fluid to be conducted by the tubing comprises the bio-compatible material.

5. The fitting element of claim 1, further comprising at least one of:
the first sealing element being removeably coupled to the tubing;
the first sealing element being fixedly coupled to the tubing; and
the first sealing element being coupled to the tubing by at least one of pressing, clipping, a direct molding process, a welding process, or a gluing process.

6. The fitting element of claim 1, wherein upon coupling the tubing to the fluidic device, the second sealing element provides a sealing stage for sealing the receiving cavity along a side of the tubing within the receiving cavity.

7. The fitting element of claim 1, further comprising at least one of:
the second sealing element comprises a front ferrule;
the second sealing element comprises a front ferrule, and the front ferrule is slidable on the tubing at least before coupling the tubing to the fluidic device;
the second sealing element comprises a front ferrule comprising a conically tapered front part configured to correspond to a conical portion of the receiving cavity of the fluidic device, wherein upon coupling the tubing to the fluidic device the conically tapered front part presses against the conical portion of the receiving cavity for sealing against the pressure in a first fluid path of the tubing;
the second sealing element is configured for sealing the receiving cavity of the fluidic device, when the receiving cavity receives the fitting element upon coupling the tubing to the fluidic device;
the second sealing element is configured for sealing the receiving cavity of the fluidic device, when the receiving cavity receives the fitting element upon coupling the tubing to the fluidic device, wherein the first sealing element is sealing the receiving cavity at the front side of the tubing, and the second sealing element is sealing the receiving cavity along a side of the tubing within the receiving cavity.

8. The fitting element of claim 1, further comprising:
a back socket surrounding the tubing in a region of an end of the tubing where the tubing is to be coupled to the fluidic device,
wherein the back socket is configured to provide mechanical support to the second sealing element exerting a force towards the tubing.

9. The fitting element of claim 1, wherein at least one of the bio-compatible materials comprises a material selected from the group consisting of a polymer, PEEK, PEKK, PE, PTFE, polyimide, a metal, gold, titanium, and a ceramic.

10. The fitting element of claim 1, further comprising at least one of:
the tubing is made of a material selected from the group consisting of a metal, stainless steel, titanium, a plastic, a polymer, glass, and quartz;
the tubing has a lumen having a diameter of less than about 0.2 mm;
the tubing has one of a circular shape, an elliptical shape, or a rectangular shape; and
the tubing is a capillary.

11. The fitting element of claim 1, comprising at least one of:
a gripping element configured for promoting, upon coupling the tubing to the fluidic device, a grip force to mechanically connect the gripping element with the tubing; and
a first joint element configured for joining to the fluidic device.

12. A fluid separation system for separating compounds of a sample fluid in a mobile phase, the fluid separation system comprising:
a mobile phase drive configured to drive a mobile phase through the fluid separation system;
a separation unit configured for separating compounds of the sample fluid in the mobile phase; and
a fitting element according to claim 1 for conducting the mobile phase to a fluidic device in the fluid separation system.

13. The fluid separation system of the claim 12, further comprising at least one of:
a sample injector configured to introduce the sample fluid into the mobile phase;
a detector configured to detect separated compounds of the sample fluid;
a collection unit configured to collect separated compounds of the sample fluid;
a data processing unit configured to process data received from the fluid separation system; and
a degassing apparatus for degassing the mobile phase.

14. The fitting element of claim 1, wherein the first sealing element at least partly covers a front side of the tubing, wherein the front side represents an axial end of the tubing.

15. The fitting element of claim 14, further comprising at least one of:
the first sealing element protrudes in an axial direction of the tubing over the front side of the tubing, at least before coupling the tubing to the fluidic device;
upon coupling the tubing to the fluidic device, the front side is fitted to the fluidic device for connecting a first fluid path of the tubing to a second fluid path of the fluidic device, and the first sealing element provides a sealing of the first and second fluid paths of the tubing and the fluidic device;
upon coupling the tubing to the fluidic device, the front side presses to a contact side of the fluidic device for coupling a first fluid path of the tubing to a second fluid path of the fluidic device;
the first sealing element is laterally extending over the front side of the tubing;
the first sealing element is laterally extending over the front side of the tubing, so that upon coupling the tubing to the fluidic device the front side represents a stopper for a forward motion of the tubing.

16. The fitting element of claim 1, wherein the first sealing element comprises an outer surface, the outer surface faces the fluidic device upon coupling, and the outer surface comprises a structure configured for increasing a surface pressure between the first sealing element and the fluidic device.

17. The fitting element of claim 16, wherein the structure comprises at least one of:
one or more indentations;
one or more concentric indentations;
one or more protrusions;

one or more concentric protrusions;

one or more micro-cavities for further acceptance of sealing components or impregnation; and one or more inclusions for further acceptance of sealing components or impregnation.

18. The fitting element of claim 1, wherein the first sealing element comprises an inlay located in a cavity of a front side of the tubing.

19. The fitting element of claim 18, further comprising at least one of:

the inlay protrudes over the front side, at least before coupling of the tubing to the fluidic device;

upon coupling of the tubing to the fluidic device, the front side is fitted to the fluidic device for connecting a first fluid path of the tubing to a second fluid path of the fluidic device, and the inlay provides a sealing of the first fluid path and the second fluid path;

the cavity is located in a center position of the front side of the tubing and opens into the flow path of the tubing.

20. The fitting element of claim 1, wherein the tubing comprises an inner tubing and an outer tubing, the outer tubing surrounding the inner tubing and providing mechanical support to the inner tubing, the inner tubing comprising a different material than the outer tubing.

21. The fitting element of claim 20, further comprising at least one of:

the inner tubing comprises the bio-compatible material;
the outer tubing comprises the first sealing element.

22. The fitting element of claim 1, further comprising a preload element configured for pressing, upon coupling the tubing to the fluidic device, the tubing in an axial direction of the tubing against the fluidic device.

23. The fitting element of claim 22, further comprising at least one of:

the preload element is configured for pressing, upon coupling the tubing to the fluidic device, a front side of the tubing in the axial direction of the tubing against the fluidic device;

the preload element exerts at least one of a spring-loaded and a spring-biased pressing force on the front side of the tubing;

the preload element is configured to promote, upon joining the tubing and the fluidic device, a forward motion of the tubing towards the fluidic device; and the preload element is configured to promote, upon joining the tubing and the fluidic device, a forward motion of the tubing towards a stopper of the tubing.

24. A fitting configured for coupling a tubing to a fluidic device, wherein the tubing comprises an inner contact surface comprising bio-compatible material, and the inner contact surface is configured to be in contact with a fluid to be conducted by the tubing, the fitting comprising:

a fitting element according to claim 1, wherein the fluidic device comprises a receiving cavity configured for receiving the fitting element, the receiving cavity comprises a receiving contact surface comprising a bio-compatible material, and upon coupling the tubing to the fluidic device, the first sealing element provides a sealing to the bio-compatible material of the inner contact surface of the tubing, the second sealing element seals against a pressure ambient to a pressure of the fluid in the tubing, and a first fluid path of the tubing is connected to a second fluid path of the fluidic device.

25. The fitting of claim 24, wherein:

the fitting element comprises a preload element, a gripping element, and a first joint element;

the receiving cavity comprises a second joint element; and upon coupling the tubing to the fluidic device, the preload element presses the tubing in an axial direction of the tubing against the fluidic device, the gripping element promotes a grip force to mechanically connect the gripping element with the tubing, and the first joint element joins to the second joint element of the fluidic device.

26. The fitting of claim 24, further comprising at least one of:

the fluidic device comprises at least one of: a second tubing, an apparatus, an HPLC device, a fluid separation device, a fluid handling device, and a measurement device;

the fluidic device comprises a processing element configured for interacting with a sample fluid;

the fluidic device is configured to conduct a sample fluid through the fluidic device;

the fluidic device is configured to analyze at least one of a physical, chemical or biological parameter of at least one compound of a sample fluid;

the fluidic device is configured to separate compounds of a sample fluid;

the fluidic device is configured to purify a sample fluid.

27. The fitting element of claim 1, wherein:

the first sealing element comprises a front socket surrounding the tubing in a region of an end of the tubing where the tubing is to be coupled to the fluidic device; and the front socket comprises a bio-compatible material and provides the sealing to the bio-compatible material of the inner contact surface of the tubing.

28. The fitting element of claim 27, wherein the front socket also comprises the second sealing element.

29. The fitting element of claim 27, wherein the second sealing element at least partly surrounds at least one of the front socket and the back socket.

* * * * *